United States Patent [19]

dePaola et al.

[11] Patent Number: 4,960,129
[45] Date of Patent: Oct. 2, 1990

[54] METHODS OF OBSERVING AUTONOMIC NEURAL STIMULATION AND DIAGNOSING CARDIAC DYNAMICAL DYSFUNCTION USING HEARTBEAT INTERVAL DATA TO ANALYZE CARDIOVENTILATORY INTERACTIONS

[75] Inventors: Robert dePaola, Philadelphia, Pa.; Stellan Ostlund, Coral Gables, Fla.

[73] Assignee: Trustees of the University of Pennsylvania, Philadelphia, Pa.

[21] Appl. No.: 280,138

[22] Filed: Dec. 5, 1988

[51] Int. Cl.⁵ .............................................. A61B 5/02
[52] U.S. Cl. .................................... 128/695; 128/700; 128/716
[58] Field of Search ............... 128/670, 695, 696, 700, 128/716, 723; 364/413.03, 413.04, 413.06

[56] References Cited
U.S. PATENT DOCUMENTS

| 4,573,472 | 5/1986 | Ito | 128/670 |
| 4,729,381 | 3/1988 | Harada et al. | 364/413.03 |
| 4,777,960 | 10/1988 | Berger | 128/670 |
| 4,781,201 | 11/1988 | Wright et al. | 364/413.03 A |
| 4,862,897 | 9/1989 | Eisenberg et al. | 128/696 |

Primary Examiner—Francis Jaworski
Assistant Examiner—George Manuel
Attorney, Agent, or Firm—Woodcock Washburn Kurtz Mackiewicz & Norris

[57] ABSTRACT

Methods of isolating individual neural impulses are disclosed. In a preferred embodiment, methods of observing the response of the heart to autonomic neural control are presented. The present invention is used to observe cardioventilatory phase-locking. The noninvasive technique disclosed are a useful clinical tool for observing phase locking as diagnostic of physiological disorders which result from autonomic neural dysfunction. The methods of observation disclosed also are applicable to the isolation of other neural impulses. An understanding of cardioventilatory interaction is obtained by plotting highly accurate heartbeat-interval (hbi) time series data versus ventilator phase. The data displays created by the methods of the present invention show structure whose features are reproducible over time and across subjects. These structures are attributable to the effect of individual neural impulses from the autonomic nervous system which influence the cardiac pacemaker. The absence of neural function has been correlated to various physiological dysfunctions.

20 Claims, 4 Drawing Sheets

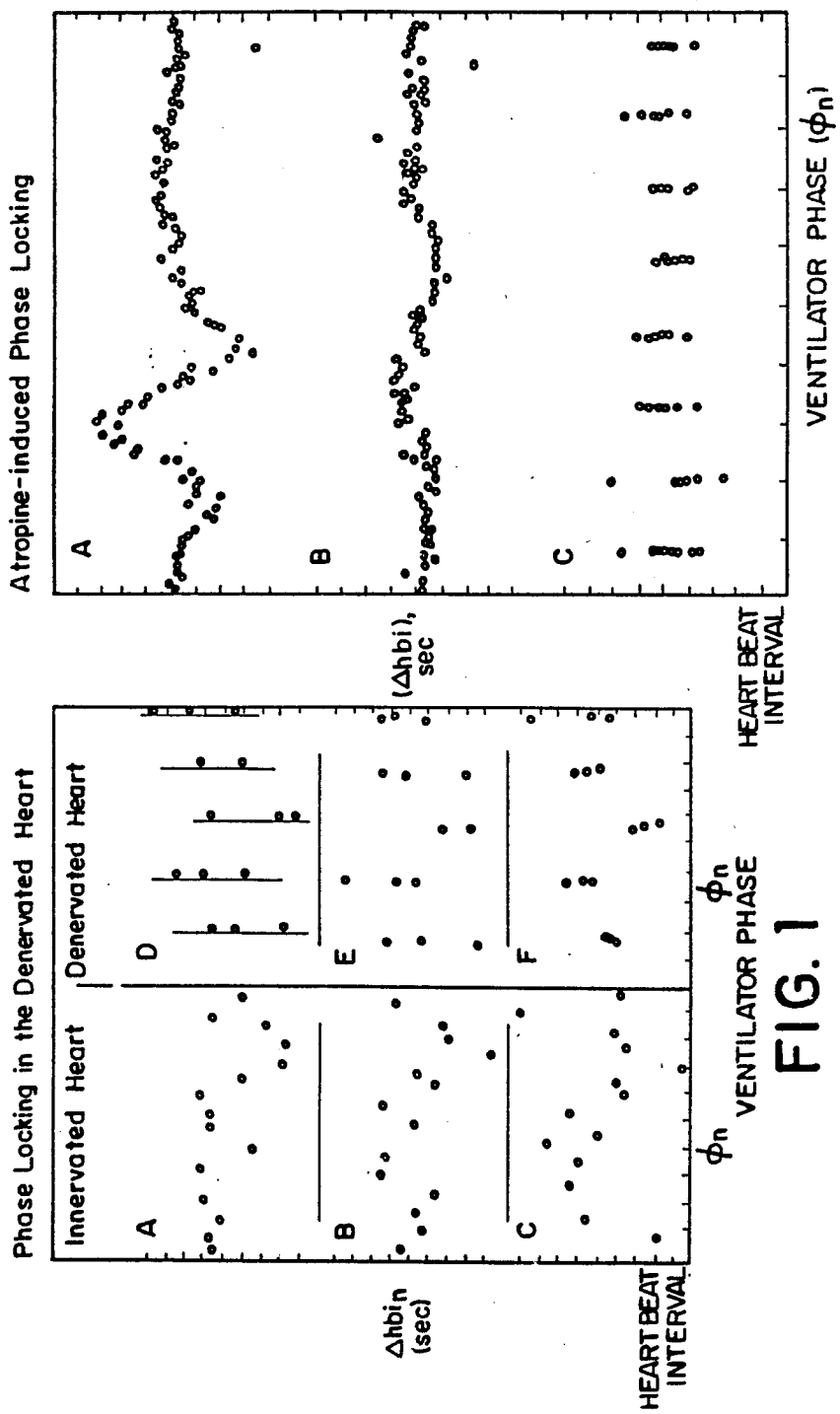

METHODS OF OBSERVING AUTONOMIC NEURAL STIMULATION AND DIAGNOSING CARDIAC DYNAMICAL DYSFUNCTION USING HEARTBEAT INTERVAL DATA TO ANALYZE CARDIOVENTILATORY INTERACTIONS

The present invention relates to methods of medical diagnosis and displaying diagnostic data. More specifically, novel methods of observing and analyzing the relationship between the ventilatory cycle and the natural pacing of the heart are disclosed. The information derived from such observations is a useful clinical tool for diagnosing autonomic neural dysfunction, natural pacemaker dysfunction, and other physiological disorders. Specific applications of these methods to isolating and observing the neural activity governing cardioventilatory interaction are also disclosed.

BACKGROUND OF THE INVENTION

It is well known that many biological systems involve rhythmic functions which repeat in an almost regular cyclic fashion. Examples of such rhythmic functions include, but are not limited to: the motion of one limb n a gait pattern, the contraction of the heart, the movement of the chest and diaphragm in respiration, the contractions of segments of the intestine, the rise and fall of populations of different species of animals within an ecosystem and the rhythmic twitching symptomatic of certain neurological disorders. Further, in many cases, it is also known (and, in other cases, it is believed) that the rates and strengths of these rhythmic functions are modulated by underlying control functions which may, in turn, be loosely related to other rhythmic functions. Examples of such phenomena are the relationships between two different limbs in a gait pattern, the effect of respiration on heart rate, the effect of small bowel contractions on rumen contractility in cows, and the interrelationship between the population cycles of predator and prey in closed ecosystems.

Perhaps the best known of these interrelated rhythmic functions is that relationship which exists between respiration and heart rate. It is well known that for the heart to function efficiently in perfusing lung and peripheral tissues, its rate and strength of contraction must be coordinated with several factors including respiration, vascular load and tissue demand for oxygen.

A cardiovascular system that is responsive to changing physiological states requires a cooperative interaction between the cardiac, ventilatory, and vascular systems. While ventilatory activity and the vascular bed are intrinsically coupled to the heart through mechanical interactions, the major factor controlling coherence in their function is the autonomic nervous system (ANS), which communicates with the cardiac pacemaker known as the sinoatrial (SA) node. Although it is widely accepted that an altered state of neural interaction with the heart accompanies a variety of pathological conditions such as congestive heart failure and diabetes, the details of this interaction remain poorly understood.

At present, the only means of understanding the effect of the autonomic nervous system is to study the aggregate effect of neural stimulation on average heart rate, since the origin of any single nerve impulse is uncertain. Since all physiological variables that contribute to the neural traffic cannot be accounted for further refinements are difficult to achieve.

Considered separately, the heart has its own series of pacemakers, the most prominent of which is the sinoatrial node (SA node), which produces an electrical depolarization which spreads throughout the heart in a coordinated way, producing a single contraction of the heart muscle--a heartbeat. The electrical signal produced by the spreading depolarization of the heart muscle can be measured at the skin surface of a subject and visually represented in an electrocardiogram (EKG or ECG). The electrical signal related to the entire cardiac cycle consists of two distinct periods: (1) the period of electrical activity when the depolarization occurs; and (2) a period of electrical quiet in between heartbeats (the interbeat interval). The measurement of this electrical signal is often used by scientists veterinarians and physicians as a means of monitoring certain cardiac and cardiovascular functions.

Much information has been accumulated about the patterns of electrical discharges through the us of EKG's. By analyzing the waveforms of single heartbeats, those skilled in the art can interpret such waveforms and make certain diagnoses based on these single heartbeat patterns. Abnormal electrical discharges originating in the ventricle of the heart, for example, are easily detected in the EKG and produce patterns in the EKG record characteristic of ventricular beats readily distinguishable from the normal beats originating from the SA node. One catastrophic condition, ventricular fibrillation, is also easily recognized in the EKG pattern.

This effect on the heart rate induced by ventilatory activity is known as respiratory sinus arrythmia. In the simplest terms, the heart rate increases on inspiration and decreases upon expiration. Research has shown that this modulation of the heartbeat is controlled through the interplay of two branches of the autonomic nervous system, which involuntarily transmits impulses to internal organs. See, A.D. Jose and R.R. Taylor, "Autonomic blockade by propanol and atropine to study intrinsic myocardial function in man", J.Clin.Inves. 48, 2019-31 (1969); J.A. Hirsch and B. Bishop, "Respiratory sinus arrythmia in humans: how breathing pattern modulates heart rate", Am.J.Physiol 241, H620-29 (1981), both of which are incorporated by reference as if fully reproduced herein. Of the two neural branches, the parasympathetic branch, which is the craniosacral portion of the autonomic nervous system, is of particular interest. It has been found that a decrease in parasympathetic activity during the inspiratory phase accounts for much of the observed increased heart rate. See, T.A. Bruce, et al., "The role of autonomic and myocardial factors in cardiac control", J.Clin.Inves. 42, no.5, 721-26 (1963); P.G. Katona, et al., "Cardiac vagal efferent activity and heart period in the carotid sinus reflex", Am.J.Physiol. 218, no. 4, 1030-37 (1970), both of which are incorporated by reference as if fully reproduced herein.

It has also long been known that the heart rate, as measured either by EKG or by pulse counting, is not constant and varies with a number of parameters. Prominent among the parameters that affect heart rate in resting subjects is the respiratory phase. Respiration itself is a variable rhythmic event under control of the central nervous system (CNS) in all animals that occurs with much slower frequencies than the heart rate. As explained above, it is known that during the relatively long inspiratory phase of respiration in normal individuals and animals, the heart rate increases and, conversely, during expiration, the heart rate decreases. However, it is further known that this alteration in heart rate occurs as a result of neural input to the SA node, principally from the parasympathetic portion of the autonomic nervous system coursing in the right vagus nerve. In persons with certain conditions, such as diabetes, heart transplants, and some forms of congenital anomalies, this increase and decrease in heart rate in loose synchrony with the inspiration and expiration is absent or minimal in magnitude. This absence of synchrony, and a belief that quantitating the effects of neural input to the heart would lead to a better understanding of cardiac function and dysfunction have resulted in a long-felt, yet unsolved need for a method of quantitating neural effects on cardiac rhythm. Those of ordinary skill recognize that more specific diagnostic and prognostic information about human and veterinary patients suffering from cardiac and other diseases can be obtained via such quantiative methods which, prior to the present invention, was unobtainable in reliable form.

The neural conduction system of the heart originates at the sinoatrial (sinus or SA) node which is located at the junction of the superior vena cava (SVC) and the right atrium. This node is the connection point for the right vagus nerve, which communicates parasympathetic neural information. At least two distinct neural components are expected to be related to the ventilatory phase. The first of these is initiated by signals transmitted to the brain by the lung and thoracic stretch receptors. These receptors generate afferent neural impulses in response to air intake during ventilation, which communicate with the sinus node via the brain stem. A second neural component originates at the carotid and atrial baroreceptors, the sensory receptors located in the arteries and within the heart which respond to pressure variations and relay signals representative of this information to the brain. The brain then transmits this information to the sinus node via the parasympathetic nervous system. This neural control of the natural pacemaker activity of a healthy heart adds great complexity to any detailed understanding of the coupling between the cardiovascular and ventilatory systems.

A crude method of determining the effects of parasympathetic nerve stimulation on heart rate, known to those skilled in the art, is to measure heart rate by counting beats under normal, at rest conditions and then comparing this rate with the observed heart rate while applying pressure to one eyeball, which is believed to induce a parasympathetic neural decrease in heart rate. It is also known, for example, that direct stimulation of the right vagus nerve will dramatically slow the heart rate in individuals with functional neural input to the SA node.

Another method, more quantitative than either of the above and applicable to human medicine, has been used by certain cardiologists and physiologists, but has met with minimal success. This method relies on frequent analysis of the electrocardiogram and of the respiratory cycle. Utilizing the principle of Fourier Analysis, the EKG is broken down into various imaginary constant components of differing frequencies and amplitudes. On of ordinary skill will readily appreciate that since the actual depolarization of the cardiac mass occurs in a regular pattern of much shorter duration than the overall cardiac cycle, the frequency components of the electrically active period in the EKG are of higher frequency than the overall cardiac cycle. Thus, changes in the heart rate are most easily observed as changes in the heartbeat interval (hbi). Consequently, in a power spectrum analysis of many sequential heartbeats, the power in the higher frequencies will be due principally to the electrical signal produced during depolarization, while the power in the lower frequencies will be more related to the interbeat interval. If the heart rate is varying considerably, the power in the lower frequencies will be spread out, while if there is no variation in heart rate (and, consequently, no variation in interbeat interval) the power in the lower frequencies will be more concentrated.

There are, however, severe deficiencies in the results obtained from this method. First, the heartbeat is not exactly periodic; since the calculations that must be performed to estimate frequency information can only be done practically through digital Fourier Transforms—which assume perfectly periodic signals—several approximations must be made in data interpretation. These approximations, however, may mask the underlying behavior of the system. Second, by using power spectral information, all phase information is lost. Since phase may be an important consideration in obtaining meaningful results, any result obtained which is unrelated to this parameter is at best incomplete. Third, because the power spectrum is dependent upon the amplitude of the electrical signal, this method is extremely sensitive to such factors as electrode placement, patient position, and disease conditions such as fluid in the chest or pericardium. Finally, these difficulties are exacerbated exponentially when similar approximations to the power spectrum are used to correlate the frequencies of the respiratory cycle with those of the cardiac cycle through ratio calculations. Thus, this method is also inadequate to fully study the effects of parasympathetic nerve stimulation on the heart.

Studies of cardioventilatory interaction typically utilize data taken on mechanically ventilated subjects. In order to provide reliable results, the extent to which the neural activity associated with free breathing has been reproduced must be determined. During both free breathing and inspiration imposed by a mechanical positive pressure ventilator, pulmonary and thoracic stretch receptors which initiate the transmission of afferent impulses to the respiratory center in the brain stem via the right and left vagus nerves are activated. From the brain stem, efferent nerve discharges are delivered through the phrenic nerve to the diaphragm and through the right vagus nerve to the SA node. This feedback mechanism results in synchronization between ventilation and the neural control of the heartbeat, whether the ventilation is naturally o externally controlled. In an artificially ventilated subject, neural activity which is normally associated with "free" breathing is essentially reproduced when the respiration is externally and consistently imposed, but this neural activity is now synchronized with the externally imposed rhythm.

The neural discharges which govern cardioventilatory interaction ar mediated through the parasympathetic branch of the autonomic nervous system. These neural discharges result in the deposition of acetylcholine at the SA node, which induces perturbations in the ion flows across the cell membranes, thus altering the excitation interval of the cardiac pacemaker. In general, the effect of the neural impulse is dependent upon the phase within the heartbeat interval at which the acetylcholine is delivered, as well as upon the heart rate and the sympathetic tone, but the result is a discrete change in the heartbeat interval which spans the neural discharge.

Therefore, although comparing neural data from mechanically respirated and naturally respirated subjects is conceptually valid, there is still a long felt but unsolved need for methods which allow neural data to be analyzed and processed, and to identify discrete neural impulses associated with specific pathologies.

Thus, it is known that the normal functioning of the cardiovascular system requires a cooperative interaction between the heart and the respiratory system. It is further known that the respiratory activity may couple directly to the heart through mechanical interactions, a condition known as phase locking. For example, there can be effects due to the local physical environment of the heart changing as the chest cavity expands during breathing. As explained at the outset, phase locking is a very general phenomenon in any dynamical system, whether physical or biological in origin. See Levy, et al., "Paradoxical effects of vagus nerve simulation of heart rate in dogs," Circ. Res., vol. 25, pp. 303-14 (1969); Jalife et al., "Dynamic vagal control of pacemaker activity in the mammalian sinoatrial node," Circ. Res., vol. 52, pp. 642-56 (1983); and Glass et al., "Global bifurcations of a periodically forced biological oscillator," Phys. RevA, vol. 29, p. 1348 (1984), all of which are incorporated by reference as if fully reproduced herein. In addition to these direct mechanical couplings, the natural pacemaker of the heart is also affected via the nervous system. The basic physiological pathways involved in this feedback loop are known; in a healthy heart there are direct repetitive neural impulses emanating from the brain stem which are synchronous with ventilation, these neural couplings are mediated through the carotid and atrial barroreceptors which have direct feedback to the SA node. The simultaneous interaction of all these influences results in a highly complex dynamical system.

OBJECTS OF THE INVENTION

It is thus an object of the present invention to provide means of quantifying and graphically representing the effect of one modulatory input system which is loosely correlated with a recordable rhythmic event upon the rate of another recordable rhythmic event in a biological system.

It is a further object of the present invention to provide a means for quantifying and graphically representing the effect of a cyclic but continuously varying modulatory neural input, derived indirectly from the respiratory cycle, on the underlying beat of the heart produced by its own irregulatory cyclic pacemaker, the SA node.

It is also an object of this invention to provide methods for identifying neural impulses associated with cardiac activity and a physiological cycle, such as the ventilatory cycle.

It is another object of this invention to provide methods for obtaining useful data from the cardio-respiratory system and to provide methods for processing and converting such data into a format which permits analysis of cardiac behavior resulting from neurological input.

It is a further object of the present invention to provide methods of displaying cardio-respiratory data in a format which reveals the presence or absence of cardioventilatory phase locking.

It is a still further object of the present invention to provide methods for presenting information useful for diagnosing and treating heart disease.

It is another object of this invention to provide methods for analyzing the effects of drugs upon the cardiac neural function.

It is also an object of this invention to provide methods for determining cardioventilatory phase locking which are incorporated into the control systems of monitoring apparatus.

SUMMARY OF THE INVENTION

The present invention presents methods and apparatus for analyzing data collected from rhythmic systems. In accordance with the present invention, data representative of a first rhythmic activity and data representative of a second substantially non-periodic rhythmic activity are concurrently collected. The first and second data collected are then processed to relate the first activity to the phase of said second activity, phase being the measure of a point in the cycle of rhythmic activity relative to its beginning and end points. Finally, a determination is made as to the presence or absence of ordered data structures indicative of the interrelationship which exists between the first and second activities.

In a preferred embodiment, cardiac and ventilatory activity of a subject ar the activities from which data is taken. In a first application, a determination is made as to whether the ordered data structure comprise substantially repetitive data points representing cardiac activity occurring at a plurality of distinct locations within the phase of the ventilatory activity, such data structures being indicative of cardioventilatory phase locking. This application of the methods of the present invention permits the examination of the effects of respiratory activity on the time interval between heart beats. Means for interpreting the processed data, such as phase maps of the difference in heart beat intervals versus the ventilator phase, are generated to allow a comparison of successive heart beat intervals and their relation to respiratory phase. These phase maps can be used to determine the presence of cardioventilatory phase locking, which has been shown to be diagnostic of cardiac neural feedback mechanisms which have been obstructed or removed. Cardioventilatory phase locking is evidenced by the grouping of values of heart beat interval difference at several locations within the ventilator phase. The existence of this type of data structure over a period of time is indicative of cardioventillatory phase locking, which may be brought about by a decrease in the neural activity which mediated the interrelationship between cardiac and ventilator activity.

In another application, a determination is made as to whether data points within a region of the phase of the ventilatory activity exhibit a substantially greater variation in the maximum and minimum data points representing cardiac activity, as compared to all other regions of the ventilatory phase; large variations within a well-defined region being indicative of neural activity.

In this application of the methods of the present invention by rigorously controlling a single variable within a rhythmic system (e.g., ventilation) and appropriately processing the data collected, the effect of neural impulses associated with particular activities and conditions can be observed in the data. In accordance with a preferred embodiment, variations of the heartbeat interval are processed by averaging these values over the ventilator phase. As long as the heart rate is not synchronized with ventilation, a plot of the differences in heartbeat interval versus respiratory phase will show sharp variation near that region of the ventilator phase where nerve impulses which are in synchrony with the ventilatory cycle arrive. The waveforms which emerge from such a plot are qualitatively similar to each other over time, independent of the precise mechanism by which the neural impulses are interpreted by the SA node. Using the methods of the present invention neural impulses which occur regularly, but which are not periodic in time can be identified. Thus, it is now possible to determine the presence or absence of particular neural impulses non-invasively, and in real time.

The methods and apparatus of the present invention therefore allow the diagnosis of these and other disorders associated with natural cardiac pacemaker and neural dysfunction, and are further applicable to the study of the effects of drugs which modify natural pacemaker activities and to other related areas of biomedical research or other clinical applications.

BRIEF DESCRIPTION OF THE DRAWINGS

FIGS. 1A-1F are six representative phase maps, created using the methods of the present invention. FIGS. 1A-1C display the behavior of a heart prior to transplantation, while FIGS. 1D-1F reveal phase-locking present in the same heart, denervated by transplantation.

FIGS. 2A-2C illustrate the behavior of a heart using phase maps generated at successive time intervals after the injection of a neural blocking drug. FIG. 2C reveals the presence of phase locking after the introduction of a neural blockade.

In FIG. 3A, the raw data representing heart beat interval and ventilator phase are shown. FIG. 3B represents a modification of the data shown in FIG. 3A.

DESCRIPTION OF THE PREFERRED EMBODIMENTS

Figure 4:
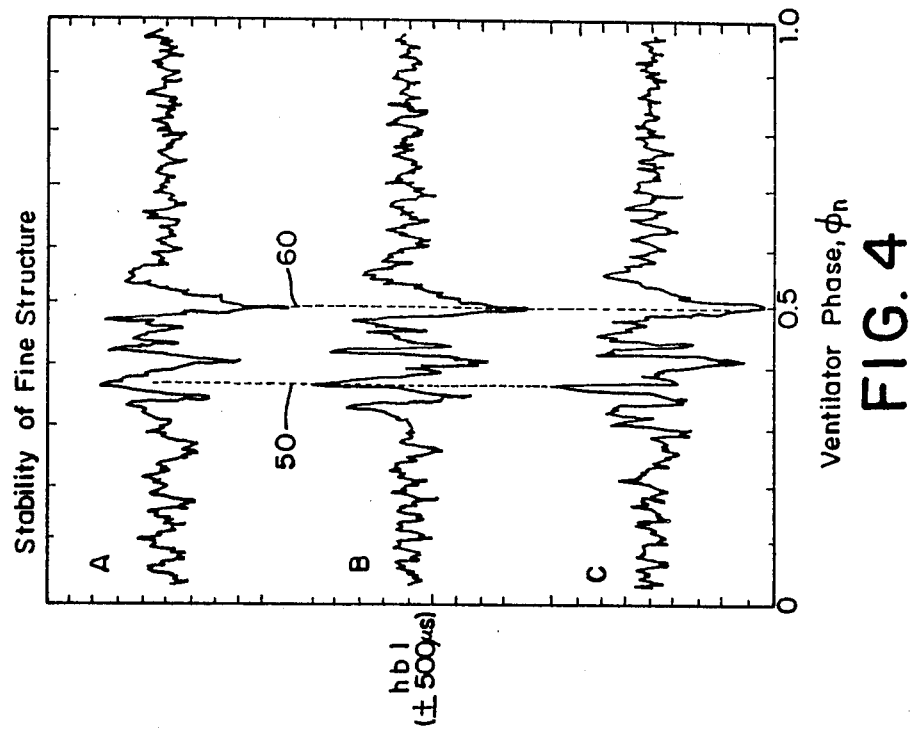
FIG. 4 illustrates three plots, successive in time. These data were overlaid in FIG. 3B. The dashed lines highlight the pronounced features which persist regularly at substantially the same ventilator phase.

The novel methods of the present invention utilize the concepts of quasiperiodic systems theory to achieve an understanding of the dynamics of cardiac rhythms. The theory of quasiperiodic systems has been applied to many dynamic systems during the last few years and important lessons have been learned about how to uncover underlying system behavior from time series data. See, D. Rand, et al., Phys.Rev.Lett. 49, 405 (1982); D. Rand, et al., Physica 5D, both of which are incorporated by reference as if fully reproduced herein.

A quasiperiodic time series contains a component called the hull function which can be used to determine the essential dynamics of the system. One preferred embodiment of the present invention discloses novel methods of uncovering a hull function describing cardiac activity from time series data. Further explanation of the application of the quasiperiodic systems theory as applied to cardiac neural control can be found in Appendix A, Appendix B, and Appendix C which are attached hereto. Preferably, the data representing the time series consists of a series of successive differences of heart-beat intervals (/ hbi), measured to about 10 microsecond accuracy.

As previously described, the normal functioning of the cardiovascular system requires a cooperative interaction between the heart and respiratory system. It is clear that respiratory activity must couple directly to the heart beat through mechanical interactions. It is also known that the natural pacemaker of the heart is affected via the parasympathetic branch of the autonomic nervous system. Therefore, the methods of the present invention are applied to show that respiratory activity must contribute a quasiperiodic component to the time series.

The hull function governing the cardioventillatory relationship is composed of several separable functions. For a given hull function, $V(x)=S(x)+N(x)+R(x)$. The first of these, $S(x)$, is described as the "smooth" component due to the direct interaction of the structure and form of the chest cavity reflected on the ECG trace, which is used to determine the interbeat interval measurement. If discrete neural activity in phase with the breathing cycle exists, there is a discontinuous or non-differentiable component, $N(x)$. Finally, there will be an apparently random component, $R(x)$, that contains activity which is either truly random or apparently random since it is decoupled from respiratory activity.

The methods for the present invention make the observation of autonomic neural activity possible by detailed measurements of its effect through the function $N(x$ described above. Quasiperiodic methods of processing time series data possess the ability to uncover information which is not necessarily periodic. This characteristic is particularly useful t the study the dynamics of physiological systems. In principle, the behavior uncovered by quasiperiodic techniques is impossible to uncover using Fourier Transform techniques, such as those previously described, due to the inherent non-periodicity of the data.

One of ordinary skill will appreciate that there are numerous systems to which the methods of the present invention are applicable. For example, neurological information derived from electroencephalographs and physiological data extracted from electrocardiograms can now be analyzed to provide diagnostic information previously unavailable. The methods presented are also particularly useful for examining a variety of rhythmic interrelations, such as those previously described. The methods of the present invention place in the hands of the physician or researcher a tool which "freezes" a particular non-periodic pattern in a manner analogous to the apparent standstill produced by a strobe light and pendulum synchronized to the same frequency. Using this new tool, the discovery and analysis of an entire class of previously hidden patterns within physiological data may now be examined, creating insights into the underlying pathologies which cause them.

As applied to the cardioventillatory system, the present invention comprises methods whereby the discontinuous component, $N(x)$, is uncovered from biological data in order to obtain a more precise picture of the neural activity associated with respiration. Previously, the overall patterns created by the three components created an indecipherable picture, of limited use as either a clinical or diagnostic tool. It is now possible to collect data and ascertain the effect of neural activity o the cardioventillatory system, by isolating the N(x) component of the hull function. Until now, the isolation and measurement of this neural traffic was only performed to a limited extent on laboratory animals and was not obtainable from human subjects.

In accordance with a preferred embodiment of the data evaluation methods of the present invention, the neural feedback mechanisms regulating the natural pacemaker are removed, either surgically or pharmacologically, and data reflecting the change in heart beat interval and ventilatory phase are collected. By correlating these data in accordance with the novel method of the present invention, it is now possible to examine the relationship between ventilation and cardiac activity. These correlated data may be analyzed for the presence or absence of cardioventilatory phase locking or other ordered data structures, such information being useful in the clinical study and diagnosis of autonomic neural dysfunction, natural pacemaker disorders, as well as other conditions.

Preferably, the data collected consist of two time series. The first, $t_n$, consists of the time of the n'the QRS complex, as measured by an electrocardiograph, preferably measured by 750,000 Hz clock to ensure sufficient data accuracy. One of ordinary skill in the art will appreciate that the QRS complex, that portion of an electrocardiogram representing the period of the depolarization of the ventricles, represents one way of obtaining these data. Other methods or apparatus which collect the same data or provide data from which this time series can be derived are equally applicable to the analysis and method of the present invention. By using the differences between successive $t_n$, the heartbeat interval, hbi, may be obtained from the equation $hbi_n = t_{n+1} - t_n$. The other data series consists of chest expansion measurements taken about every 0.25 seconds using the digitized output of an impedance plethysmograph. An impedance plethysmograph measures volume changes in terms of the change in bulk impedance between electrodes placed at two or more points on the skin surface. The chest expansion measurements are thereby used to obtain the ventilator frequency converted to the units of $t_n$. Using the frequency thus obtained, it is now possible to compute the ventilatory phase, $\emptyset_n$, corresponding to each $t_n$. The ventilatory phase is defined as the fractional part or modulus of the ventilatory cycle corresponding to a period normalized between 0 and 1. One of ordinary skill in the art will realize that similar data may be provided by other methods of plethysmography, or derived from other physiological data to obtain the necessary ventilatory phase data.

Thus, two columns of data are acquired, $\emptyset_n$ and $hbi_n$, which represent a transformation of the raw data. In order to minimize the effect of long term drifts in heart rate, the present invention utilizes the difference in heartbeat intervals between successive beats as a dependent variable, i.e., $/hbi = hbi_{n+1} - hbi_n$.

In order to utilize the information generated by processing the collected data, $/hbi$ vs. $\emptyset_n$ are plotted on an X—Y coordinate system. The resulting novel scatterplot is defined as a "ventilator phase map"; from these phase maps useful information relating to the neural control of the heart may be obtained. It has been found that specific types of scatterplots can be related to the presence or absence of neural signals. For example, as will be explained in detail below, cardio-pulmonary phase-locking can be detected through the use of these scatterplots. The scatterplots of the present invention have also been used to identify the presence or absence of synaptically transmitted neural input to the natural pacemaker. Thus, from the user's perspective, the present invention provides of a set of data, which may be displayed for visual analysis or processed electronically to identify specific occurrences of linearity among the data sets or recurrences of specific patterns within a portion of the ventilator phase. In the case of visual display, a clinician or researcher may observe patterns such as those appearing in FIGS. 1-5 in real time. One of ordinary skill will realize that data storage and retrieval means will permit the overlaying and comparison of data from differing time periods, either by generating scatterplots or performing such comparisons via electronic computing means and determining the presence or existence of certain pre-determined patterns or conditions.

The present invention contemplates that the phase maps generated by the methods disclosed may be classified by those skilled in the art to correspond to differing cardiac conditions and dysfunctions. Through this process, a base of empirical knowledge will be developed, allowing the phase maps of the present invention to provide a deeper understanding of the complex dynamical interactions present in cardiac activity. Thus, in the same manner as electrocardiograms or X-ray films, the phase plots of the present invention can be "read" by those of sufficient training and experience to determine if a patient is suffering from a particular condition.

One of ordinary skill will appreciate the usefulness of the ventilator phase maps disclosed above. The following examples of this method of data representation are illustrative, however, the present invention is not limited to the Examples described.

EXAMPLE I

The following Example may be more fully understood by reference to the drawings, particularly FIG. 1A-1F.

The methods of the present invention are used to collect data and create phase maps which allow a comparison of the cardioventilatory relationship in innervated and denervated hearts. The denervated condition studied results from transplantation, however, the results obtained provide useful information for observing all cardiac activity.

FIGS. 1A-1F illustrate ventilator phase maps obtained from innervated and denervated hearts. All surgical investigations were performed on piglets weighing about 2-3 kg, mechanically ventilated at ventilatory rates of about 16-24 breaths per minute, tidal volumes of about 10-15 ml/kg, and inspiratory times typically about 0.06 seconds. In all studies, data trains were obtained via surface ECG leads simultaneously with those obtained using epicardial leads.

Data collected from innervated hearts is illustrated in FIGS. 1A-1C. These phase maps comprise consecutive 15 point data segments taken from the innervated (donor) heart. The plots obtained typify maps obtained from the recipient heart prior to transplantation, as well as from all innervated animal and human hearts studied thus far.

The same data were collected from the same heart following transplantation. These results are illustrated in FIGS. 1D-1F. A comparison of these two sets of phase maps (1A–1C and 1D–1F) illustrates the differences in the dynamics of the two systems. It is apparent that in the absence of autonomic neural control, the heartbeat is initiated only at well defined points within the ventilatory phase. It is further apparent that there is small integer ratio of heartbeat interval to ventilator period (hbi$_n$/$\emptyset_n$). This behavior is described as cardioventilatory phase locking. FIGS. 1D–1F reveal a 5:1 phase lock, reflecting a heart rate five times the ventilatory rate. In contrast, the plots shown in FIGS. 1A–1C demonstrate that a normally functioning innervated heart initiates heartbeats at arbitrary phases within the ventilatory cycle. Normally functioning hearts only exhibit low-order phase locking for rare, transitory periods of time; the denervated hearts exhibit this phenomenon for extended periods, on the order of twenty minutes, before shifting to different, but similar, low order locking ratios in response to drifts in the average heart rate.

EXAMPLE II

The autonomic neural control of the heart may be inhibited pharmacologically by anticholinergic drugs such as atropine. Pharmacological investigations were performed on piglets under conditions similar to those described in Example I. The piglets were anesthetized with about 25–30 mg/kg Phenobarbital and paralyzed with about 0.100 mg/kg Pancuronium Bromide. In all studies, data trains were obtained via surface ECG leads simultaneously with those obtained using epicardial leads.

Atropine competitively inhibits postganglionic parasympathetic receptors, attenuating via vagal blockade the parasympathetic input to the sinus node which is coincident with ventilatory activity. Thus, the administration of atropine is used as an alternative way of examining the effects of isolating the heart from neural stimuli, without resorting to surgical denervation, as illustrated in Example I.

The data for this example were continuously collected while administering about a 0.04 mg/kg bolus of atropine to a piglet. The resulting phase maps, generated by the methods of the present invention previously described, are illustrated in FIG. 2. The phase maps presented in FIG. 2 represent one hundred heartbeat intervals, measured at discrete periods of time. The phase map shown in FIG. 2A is representative of a typical innervated heart and represents data taken just prior to the introduction of atropine into the piglet's system. FIG. 2B illustrates a transitional state, forty-five seconds after injection, which is characterized by a reduction in the amplitude of the dominant sinusoidal structure. This amplitude is closely associated with respiratory sinus arrythmia (RSA), and as phase maps and other data are collected, the presence of this feature will provide an empirical body of diagnostic information about the subject's condition. The condition two minutes after injection is illustrated in FIG. 2C, which is typical of the condition maintained for the next thirty minutes. As for the surgically denervated hearts discussed in Example I, the pharmacologically denervated heart exhibits low order phase-locking, in this case an 8:1 ratio.

DISCUSSION OF EXAMPLES I AND II

Generally, in a system with two frequencies, phase locking is expected. As the foregoing Examples illustrate, such a system is the cardioventilatory system, where one frequency results from respiration and the other from cardiac activity. The absence of low order phase locking in a normally functioning subject is indicative of a highly specialized feedback system which acts to frustrate this phase locking.

It has been now shown that persistent low order cardioventilatory phase locking is observed in post-transplant subjects and in subjects following parasympathetic blockade, and further that low order phase locking is absent in subjects with unaltered cardiac parasympathetic feedback. Therefore, it has now been discovered that low order phase locking of the heartbeat to ventilation is diagnostic of cardiac neural feedback mechanisms which have been obstructed, removed or are deteriorating. The present invention presents methods of extracting an displaying this information as a valuable clinical and diagnostic tool to further the study of this complex physiological system.

EXAMPLE III

Figure 3:
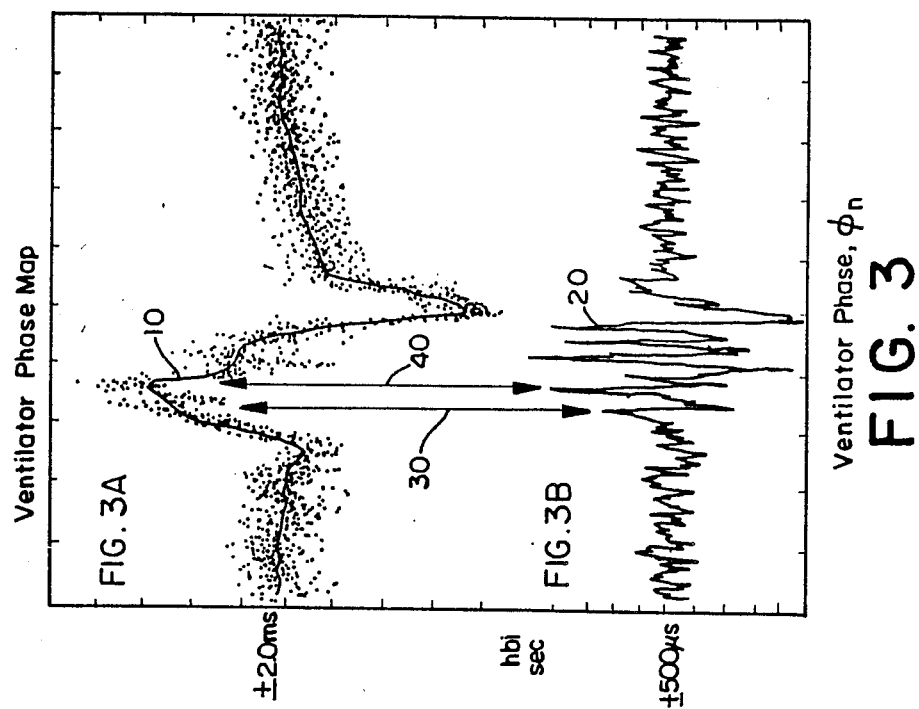
FIGS. 3A-3C illustrate data from which ventilator phase maps are generated.
Figure 5:
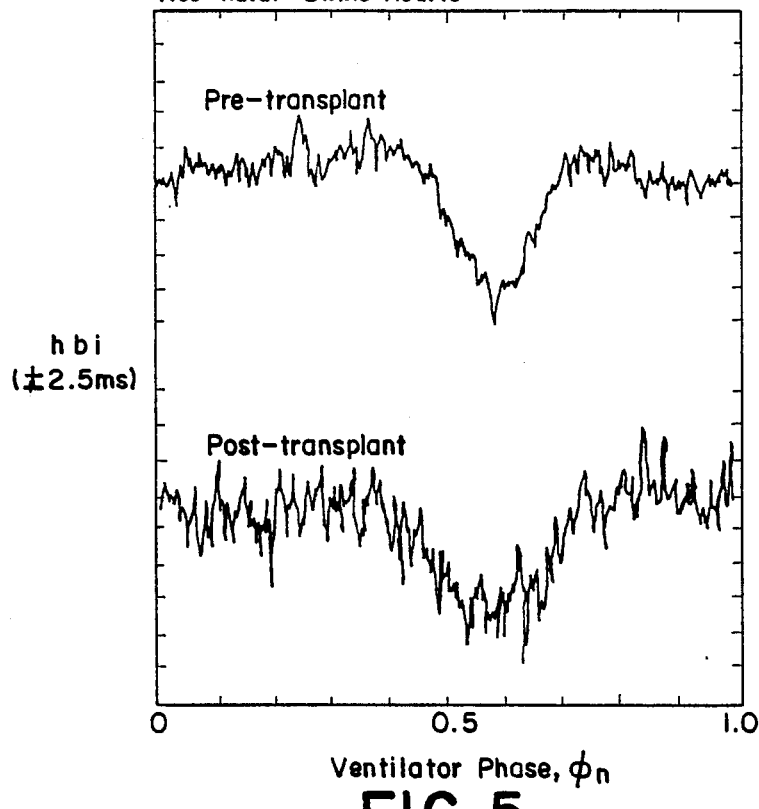
FIG. 5A and 5B illustrate a comparison of phase maps taken from innervated (FIG. 5A, pre-transplant) and denervated (FIG. 5B, post-transplant) hearts.

Further illustration of the methods of the application of the present invention are best are best understood by reference to FIGS. 3–5.

Referring to FIG. 3A, there is illustrated a ventilator phase map of a mechanically ventilated infant created using the methods of the present invention. The data represent 3072 points gathered over a period of 17 minutes during which the average heart rate was gradually decreasing from 185–178 beats per minute. Several important characteristics can be seen in this plot. The most apparent characteristic can be called the "broad structure", an envelope which varies substantially sinusoidally with one cycle of the ventilator. This broad structure of the respirator phase map results from the mechanical coupling between the respiratory and the cardiovascular systems, which is described by the S(x) component of the hull function, as explained above. Within this envelope, there are a series of very pronounced deviations from the mean (i.e., "sharp jags"). These are called the "fine structure", and are attributed to the N(x) component. The fine structure is specifically related to neural activity that correlates to the exigencies of the system being studied. All other variation is described as "apparent noise". The adjective "apparent"is used, since these signals could be very regular in time, but are not synchronized to the ventilator, and thus cannot be distinguished from measurement uncertainty.

The broad structure is closely related to the respiratory sinus arrhythmia (RSA) which has been found to result from a variety of mechanical and neural couplings between the pulmonary and cardiovascular systems. The variation in the chest cavity during respiration influences the heart rate both by affecting the carotid and atrial baroreceptors in the heart which sense blood pressure, and also leads to an apparent variation of heart rate due to shift in the underlying tissue through which a signal must propagate to reach the surface electrodes of the ECG.

The present invention provides methods by which the fine structure may be examined, thereby providing important data about the underlying physiological interactions. Fine structure similar to that illustrated in FIG. 3A is visible in most subjects and is more pronounced during periods when the heart rate is slowing down. In order to examine the fine structure in more detail the original remapped data, which appears in FIG. 3A, is subtracted from a running average of enough data points to remove substantially all variations shorter than about 1/20 of a ventilator cycle. This corresponds to about a 150 point running average, drawn with the solid line 10 shown in FIG. 3A. The difference (residues) of the data points relative to this running average is shown in FIG. 3B as line 20. Since no readily apparent pattern occurs in the data on time scales less than 1/100 of a ventilator cycle, a 30 point running average of the residues is performed to highlight the features of a fine structure. Effectively, a band-pass filter is created between frequencies of 1/20 and 1/100 of the ventilator cycle to smooth the data. Referring to FIG. 3A-3B, the vertical lines 30,40 highlight the close correspondence between fine structure features visible directly in the ventilator phase map illustrated in FIG. 3A and extracted in the smoothed data as shown in FIG. 3B. Although it may appear that less pronounced fine structure is present in the rest of the smoothed plot as well, one of ordinary skill in the art will appreciate that smoothed random data will also show structure. However, the methods of the present invention extract those structures which have physiological importance.

Since random fluctuations are not stable in time, those of physiological origin will persist across time in successive plots created using the methods disclosed. Only the major features in the fine structure map are stable in time, therefore, much significance cannot be attached to transitory structures which appear in the flat regions of the phase maps adjacent the prominent fine structure.

Referring now to FIG. 3B, it can be seen that the fine structure is confined to a small portion of the ventilator phase. The term 'ventilator phase' describes a complete ventilatory cycled derived from pressure or other data, and normalized from 0 to 1 (i.e., immediately after that portion of the ventilator phase denominated as 1, the ventilatory cycle will again be at "0"). The region of the fine structure corresponds to that portion of the ventilator phase between about 0.2930–0.4301, which represents about 15% of the ventilator cycle. The fine structure features are substantially equally spaced. Based on the distance between the five most prominent sequential features, a spacing of about 0.01719±0.0006 phase units can be estimated. Since the patient from which these data have been taken was ventilated at a rate of 12.1356 breaths per min., this spacing corresponds to 85±3 ms. This spacing is typical of what is observed in all human infants and neo-natal swine studied.

FIG. 4 illustrates three plots of the "fine structure" maps of three successive 1024 point data streams which comprise that of the single ma presented in FIG. 3B. FIG. 4 demonstrates the stability over time of the fine structure since it is generally located in the region of the dashed lines 50, 60 shown. In each plot, a 30 point running average is subtracted from the original remapped data and a 10 point running smooth average is performed on the residues. It should be noted that the positions of the dominant fine structure remain stable throughout time, despite the variation of the heart rate from 178 bpm to 185 bpm, which corresponds a variation ten times the full scale in the residue plots. The stability of the location of these fine structure peaks is remarkable. A review of infant and animal data reveals that the positions of the fine structure can be consistent over time intervals of more than one hour, and are most pronounced when the heart rate is gradually decreasing. The time interval between fine structure features is typically 50-150 ms, but within a given subject, it is stable to a few percent. Because this time scale corresponds to estimates of the interval between nerve impulses arriving at the SA node which modulate the heart rate in response to increased breathing rate, it is apparent that the "fine structure" results from the cardiac response to the synaptically transmitted neural input to the cardiac pacemaker.

The methods of the present invention therefore present a principle of diagnosis by identifying the existence of the fine structure. It has now been found that the occurrence of the fine structure is not periodic, i.e., regular in time, but instead can be related to another system parameter, such as ventilator phase. It has been found that while the fine structure does not appear during every cycle, when it does appear, its location relative to the phase can be accurately predicted. This information can then be related to the condition of the patient being studied to provide diagnostic information.

In order to test whether the fine structure is of neural origin, ventilator phase maps were constructed before and after disconnecting the neural input to the heart. This denervation can effectively be accomplished by transplanting the heart to another subject. The pre- and post-transplant hearts are referred to respectively as "neurally connected" and "neurally disconnected".

Ventilator phase maps, subjected to a 10 point running average, which have been computed both before and after transplantation of a neo-natal swine heart are illustrated FIGS. 5A–5B. Data collected from the donor heart, before transplantation, are shown in FIG. 5A, while FIG. 5B illustrates data from the same heart after transplantation. One of ordinary skill can observe that FIG. 5A is substantially similar in appearance to FIG. 3A. Further, it has been found that FIG. 5A is typical of the maps obtained from all neurally connected hearts examined. As shown in FIG. 3A, referred to in Example II above, the broad structure region of the phase map also contains fine structure whose positions are time independent, while the flat region contains structure which is transitory over a time scale of minutes. Noise, as estimated by the standard deviation from a 5the degree polynomial fit in each of the regions, is typically three times lower in the broad structure region than in the flat areas of the map.

The ventilator phase maps of the neurally disconnected (transplant) heart, illustrated in FIG. 5B, are substantially different in appearance from maps obtained before transplantation. First, the apparent noise is considerably higher for neurally connected hearts than for the disconnected hearts. Second, within a single plot, the noise levels (the overall variation in hbi) in both the coupled and uncoupled regions are of comparable magnitude. Finally, all the structure in both the coupled and uncoupled regions is transitory over a time scale of minutes. The existence of this completely transitory structure indicates that the substantially non-transitory fine structure observed in the connected heart is related to neural activity.

DISCUSSION OF EXAMPLE III

In both human and animal studies a considerable variability in the shape of the broad structure is observed, due in large part to the harmonics introduced via the mechanical ventilator-pulmonary coupling. The differences in the overall shape between the broad structure of FIG. 3A and that of FIG. 5A reflect different mechanical couplings between the respective ventilator and pulmonary system of each subject.

The conclusion that the observed fine structure reflects the cardiac response to the synaptically transmitted neural input to the natural pacemaker is based on the following evidence:

The fine structure is stable over time and subject.

The fine structure is absent from all hearts which have been disconnected from the autonomic nervous system.

The observation that the fine structure is most pronounced during heart rate deceleration is consistent with accepted physiological models which attribute the slowing down of the heart rate to increased parasympathetic neural activity.

The time scale at which the fine structure is observed is inconsistent with a mechanical interaction.

Additionally, as noted above, while there is a substantial correlation between the presence of the fine structure and the deceleration of the heart rate, there is no indication any such correlation to ventilator parameters.

Accordingly, a model of the response of the heart to control by impulses of the autonomic nervous system associated with ventilation, reflected in the ventilator phase maps, can be derived using the methods presented by the present invention. In the broad structure regions of the phase maps, the presence of neural pulses which are in phase with ventilation impose a discrete time independent structure, since the period of SA nodal excitation can only be discretely altered at certain well defined phases in the respiratory cycle. Over time, the statistical accumulation of these SA node excitations at the imposed phases are reflected by the presence of fine structure superimposed on a relatively smooth background. In the absence of neural control associated with ventilation, no identifiable preferred phases exist and the SA node excitations are distributed randomly within the ventilator phase axis; this is evidenced by transitory structure. Provided that the signals still exist and become uncorrelated to respiration, the randomness of the transitory structure accounts for the higher noise levels visible in flat regions of the maps.

REMARKS REGARDING EXAMPLES

The present invention demonstrates methods providing the ability to directly observe the response of the heart to neural autonomic nervous system respiratory control. These methods are a major breakthrough in the study of cardiac behavior; in addition to providing a valuable new research tool, potential applications of this technique range from the diagnosis and treatment of neurologically-based heart disease to the development of new medications.

One skilled in the art will realize that the methods of the present invention represent new and useful techniques of processing data to uncover the presence of cardioventilatory phase locking and other phenomena. Applications of this invention are not limited to the visual display of the phase maps. The methods of the present invention are useful, for example, by incorporation into the control system apparatus of a medical device, and can be used in conjunction with a microprocessor or other computational means to implement a medical process or provide a perceptible indication upon the initiation of cardioventilatory phase locking or the detection of other specific neural activity.

It is widely accepted that an altered state of neural interaction with the heart accompanies a variety of pathological conditions such as congestive heart failure and diabetes. Though it is not known to what extent these pathologies relate to a complete breakdown of the parasympathetic communication to the cardiac sinus node, it is known that such a breakdown may adversely effect the health of the patient because it disables the heart from immediately responding to the body's physiological demands. Additionally, because the loss of neurological control of the heart rate must inhibit a cardiac patient's ability to respond to stress, the observation of cardioventilatory phase locking can provide an early warning of cardiac failure before the stress is present. The present invention discloses methods of observing conditions such as cardioventilatory phase locking noninvasively. The discovery of this method provides a valuable clinical tool for the diagnosis of all physiological disorders whose symptoms include neurological dysfunction.

METHODS AND APPARATUS

Figure 6:
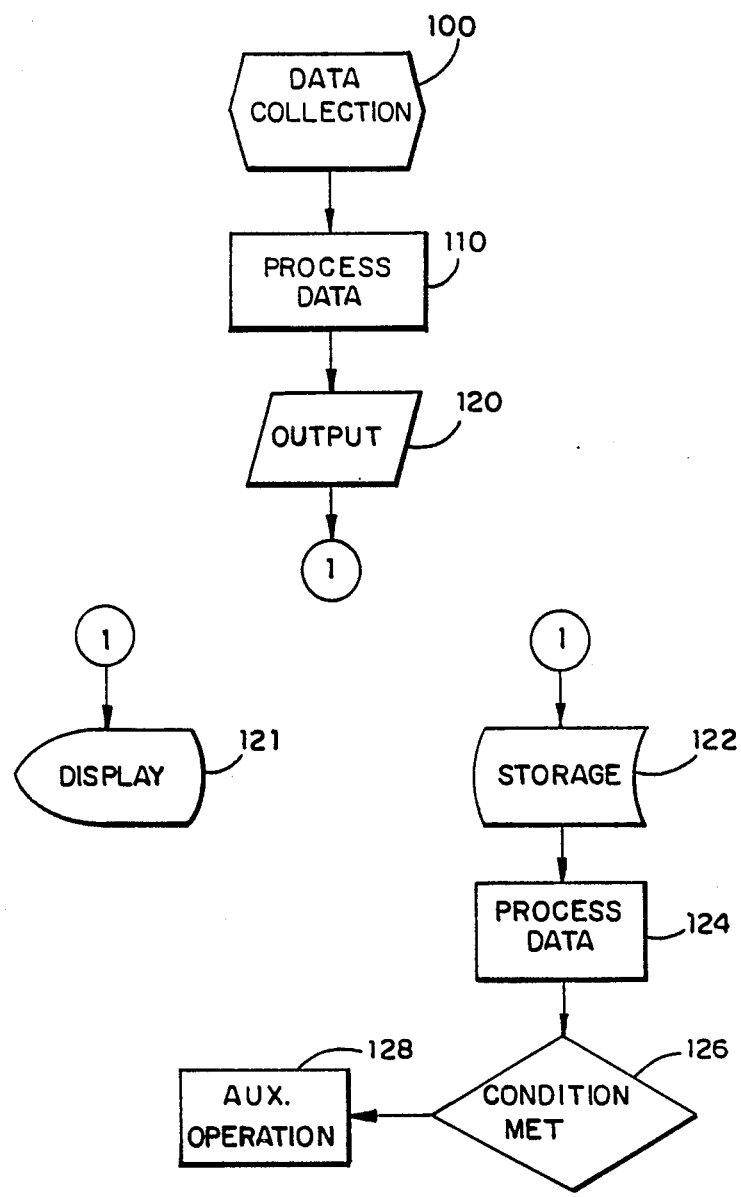
FIG. 6 is a simplified flowchart of a method of the present invention.

Referring to FIG. 6, there is illustrated a simplified flow chart describing the method steps of the present invention. Data collection 100, in the case of the cardioventilatory system comprise means for collecting heart beat interval and ventilation frequency data. In other rhythmic systems, the data collection step 100 comprises collecting timing interval data describing a first cycle and frequency data representative of another cycle which influences the first. Once the time series data are collected, a processing step 110 converts the data to a form which reflects the influence of the cycles upon on another. For example, it has been found that comparing heartbeat interval data to ventilatory phase provides meaningful results. The processed data is then transmitted to an output 120. The output 120 may alternatively connect to a display means 121, or to storage means 122. In the second alternative, the stored data is be further processed at 124, and compared with other data or reference data to determine if a specified condition has been met. In the example of cardioventilatory phase locking, this condition is the linearity and ordering of the processed data. Finally, if the condition is met, an auxiliary operation 128 may be performed. The auxiliary operation consists of triggering other apparatus to act upon the subject, activating recording or display means, or notifying an operator that the condition has been met.

Figure 7:
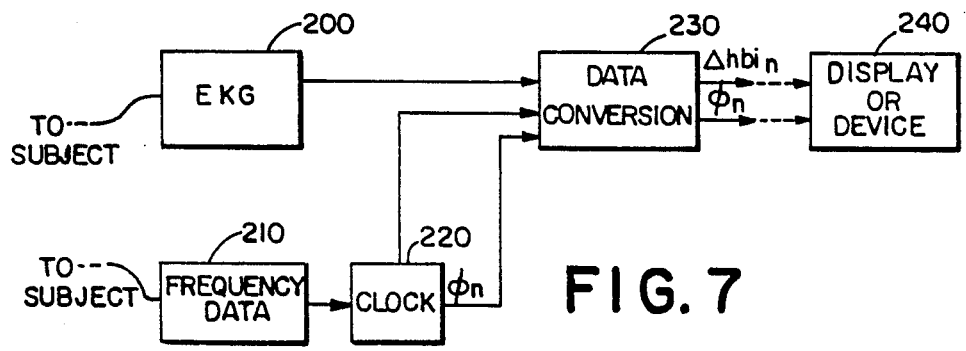
FIG. 7 illustrates a simplified block diagram of preferred for carrying out the present invention.

In FIG. 7, there is illustrated a simplified block diagram of a preferred apparatus for carrying out the present invention, as applied to the cardioventillatory system, as discussed in the Examples above. Electrocardiogram apparatus 200 or other means for determining heartbeat intervals and means for collecting ventilator frequency 210 are connected to a subject. A clock 220 is provided which is used to convert the frequency data to phase data and also to correlate the heartbeat interval data contained in the EKG signal to time. The heartbeat interval, time and phase data are processed and converted at 230 into a suitable format, such as shown in FIGS. 1-5, for either display 240 or input into another device 240. The secondary device 240 may be simply a storage medium or may be another apparatus which uses the data from the apparatus described to perform other functions, such as activating equipment or alerting an operator of the subject's condition.

What is claimed is:

1. A method of determining the occurrence of a neural stimulus to a cyclic physiological function which occurs in a subject, comprising the steps of:
  (a) determining the time interval between successive heartbeats of said subject and generating data representative of said time intervals;
  (b) determining the phase of said cyclic physiological function over a predetermined interval concurrent with said time interval determination, said interval having a duration of more than one heartbeat, and generating data representative of said phase;
  (c) combining said heartbeat interval and physiological phase data as a data set;
  (d) processing said data set to identify pronounced variations in said heartbeat interval data within a portion of said cycle of said physiological function;
  whereby the presence of said repetitive pronounced variation is indicative of the occurrence of neural stimulus.

2. The method of claim 1, further comprising the steps of:
  (e) further processing said time interval data to remove substantially all of said variations having a duration less than about five percent (5%) of said cycle;
  (f) further processing said time interval data to collect all of said variations having a duration greater than about one percent (1%) of said cycle;
  (g) storing time interval data processed according to steps (e)-(f) as a final data set;
  (h) collecting a plurality of said final data sets, taken successively from said subject; and
  (i) displaying said plurality of final data sets in a manner to indicate the presence of a repetitive pronounced variation within an identified portion of said physiological cycle;
  whereby the neural stimulation of said physiological cycle is indicated.

3. The method of claim 2, wherein:
  (a) said further processing of step (e) comprises performing a 150 point running average on said data set; and
  (b) said further processing of step (f) comprises performing a 30 point running average to obtain a final data set.

4. The method of claim 1, wherein said physiological cycle is the ventilatory cycle of said subject.

5. A method of observing cardiac neural stimulus in a subject, comprising the steps of:
  (a) determining the time interval between successive heartbeats of said subject and generating data representative of said time intervals;
  (b) determining the frequency of a cycle of a physiological function of said subject over a predetermined interval concurrent with said time interval determination, said interval having a duration of more than one heartbeat, and generating data representative of said frequency;
  (c) combining said heartbeat interval and physiological frequency data as a data set;
  (d) processing said data set through a band pass filter, wherein said band pass filter is designed to operate at frequencies between about 1/20 and about 1/100 of said physiological cycle to obtain a final data set;
  (e) collecting a plurality of said final data sets, taken successively in time from said subject; and
  (f) displaying said plurality of final data sets in a manner to indicate the presence of a repetitive pronounced variation within a particular portion of said physiological cycle.

6. The method of claim 5, wherein said physiological cycle is the ventilatory cycle of said subject.

7. A method of identifying cardiac neurological dysfunction in a subject, comprising the steps of:
  (a) determining the time interval between successive heartbeats of said subject and generating data representative of said time intervals;
  (b) determining the frequency of ventilation of said subject over a predetermined interval concurrent with said time interval determination which coincides with a plurality of said heartbeats, and generating data representative of said frequency;
  (c) combining said heartbeat interval and ventilatory frequency data as a data set;
  (d) processing said data set to determine the presence or absence of cardioventilatory phase locking; and
  (e) displaying said data in a manner to indicate the presence or absence of said phase locking, the presence of phase locking being indicative of neural dysfunction.

8. The method of claim 7 further comprising the steps of:
  (f) converting said frequency to a ventilatory phase related to said interval between beats of a heart; and
  (g) calculating the difference between successive heartbeat intervals.

9. The method of claim 8 further comprising the step of:
  (h) displaying said ventilatory phase and said difference between successive heartbeat intervals upon a coordinate system, having at least two axes, wherein said ventilatory phase is displayed upon one of said axes as the dependent variable, said data being displayed in a manner to indicate the presence or absence of group of closely spaced data points wherein said groups form substantially straight, substantially parallel lines when interconnected.

10. The method of claim 7 wherein steps (a)-(e) are performed in real time.

11. A method for determining the presence of cardioventilatory phase locking in a subject, comprising the steps of:
  (a) acquiring data representing the respective time intervals between successive heartbeats of said subject;
  (b) concurrently acquiring data representing the phase of the ventilatory cycle of said subject related to said heartbeat interval data;
  (c) determining whether said data acquired in steps (a) and (b) are substantially linearly correlated at substantially the same point in the ventilatory cycle of said subject over a discrete period of time;
  whereby the existence of said substantial linear correlation is indicative of cardioventilatory phase locking.

12. The method of claim 11, wherein the step of determining whether substantial linear correlation described in step (c) is present is comprised of creating an observable representation of a display of said data and visually inspecting said observable representation.

13. In a patient having a heart and at least one other organ exhibiting a regularly recurring physiological cycle, apparatus for observing cardiac neural stimulus in the patient comprising:

(a) means for determining heartbeat data representative of the time interval between successive heartbeats of said patient;
(b) means for determining frequency data representative of the frequency of said regularly recurring physiological cycle of said at least one other organ of said patient over a period of time concurrent with said successive heartbeats; and
(c) computing means for combining said heartbeat data and said frequency data and for processing said combined data to determine the presence of a repetitive pronounced variation of said regularly recurring physiological cycle and identify the a particular portion of said physiological cycle said pronounced variation occurs.

14. The apparatus of claim 13, further comprising display means for displaying said data and indicating the presence of said repetitive pronounced variation within a particular portion of said physiological cycle.

15. Apparatus for cardiac and ventilatory monitoring of a patient, comprising:
(a) means for determining data representative of the time interval between successive heartbeats of said patient;
(b) means for determining data representative of the frequency of ventilation of said patient over a period of time including said successive heartbeats; and
(c) computing means for combining said heartbeat data and said ventilation data to create a combined data set and means for processing said combined data set to determine the presence and/or absence of cardioventilatory phase locking.

16. The apparatus of claim 15, further comprising means for displaying said combined data set so as to indicate the presence and/or absence of said phase locking.

17. A method of analyzing data collected from rhythmic systems, comprising the steps of:
(a) collecting first data representative of a first nonperiodic rhythmic activity;
(b) collecting second data representative of a second rhythmic activity concurrently with said first data; said second activity having an interrelationship with said first activity;
(c) processing said first and second data to relate said first activity to the phase of said second activity; and
(d) determining the existence of ordered data structures indicative of the interrelationship between said first and second activities.

18. The method of claim 17, wherein said first activity is the ventilatory activity of a subject and said second activity is the cardiac activity of a subject.

19. The method of claim 18, wherein said ordered data structures comprise substantially repetitive data points representing said cardiac activity said data points occurring at plurality of distinct locations within the phase of said ventilatory activity; whereby said data structures are indicative of cardioventilatory phase locking.

20. The method of claim 18, wherein said ordered data structures comprise data values within a region of the phase of said ventilatory activity exhibiting a substantially greater variation in the maximum and minimum data points representing cardiac activity than all other regions of said ventilatory phase; whereby said data structures represent the existence of neural activity.

* * * * *